(12) United States Patent
Lu

(10) Patent No.: US 7,083,912 B2
(45) Date of Patent: Aug. 1, 2006

(54) MAB-BASED DOT-ELISA METHOD AND ASSAY KIT FOR THE DETECTION OF VIRUSES

(75) Inventor: Huanguang Lu, State College, PA (US)

(73) Assignee: Penn State Research Foundation, University Park, PA (US)

( * ) Notice: Subject to any disclaimer, the term of this patent is extended or adjusted under 35 U.S.C. 154(b) by 70 days.

(21) Appl. No.: 10/448,333

(22) Filed: May 30, 2003

(65) Prior Publication Data

US 2006/0105328 A1    May 18, 2006

Related U.S. Application Data

(60) Provisional application No. 60/385,841, filed on May 31, 2002.

(51) Int. Cl.
*C12Q 1/70* (2006.01)
(52) U.S. Cl. ............... 435/5; 435/7.1; 435/962; 436/518
(58) Field of Classification Search ............... 435/5, 435/7.1, 962; 436/518
See application file for complete search history.

(56) References Cited

U.S. PATENT DOCUMENTS

| | | | |
|---|---|---|---|
| 4,281,061 A * | 7/1981 | Zuk et al. ............... | 435/7.9 |
| 4,302,444 A | 11/1981 | Baxendale | |
| 4,643,578 A | 2/1987 | Stern | |
| 4,855,408 A | 8/1989 | Kuhn et al. | |
| 4,942,126 A | 7/1990 | Slifkin | |
| 5,173,737 A | 12/1992 | Mitchell et al. | |
| 5,174,993 A | 12/1992 | Paoletti | |
| 5,196,514 A | 3/1993 | Avakian et al. | |
| 5,494,801 A * | 2/1996 | Bogart et al. ............... | 435/7.34 |
| 5,597,735 A | 1/1997 | Laszlo et al. | |
| 5,773,212 A * | 6/1998 | Figard ............... | 435/5 |
| 5,916,879 A | 6/1999 | Webster | |
| 5,989,805 A | 11/1999 | Reilly et al. | |
| 6,033,670 A | 3/2000 | Bublot et al. | |
| 6,265,176 B1 | 7/2001 | Lin et al. | |
| 6,297,062 B1 | 10/2001 | Gombinski | |
| 6,465,171 B1 | 10/2002 | Goebel et al. | |
| 6,492,166 B1 | 12/2002 | Ferris et al. | |
| 6,506,385 B1 | 1/2003 | Poston et al. | |
| 2003/0186285 A1 * | 10/2003 | Saito et al. ............... | 435/6 |

OTHER PUBLICATIONS

Schleicher & Schuell "Transfer and Immobilization of Proteins to S&S Solid Supports", published by Schleicher & Schuell, Inc., 1981, p. 7.*
Aldrich Catalog, 1001 West Saint Paul Ave, Milwaukee, WI, 53233, 1996, p. 1511.*
James L. Bennington, Saunders Dictionary & Encyclopedia of Laboratory Medicine and Technology, Philadelphia, PA, W.B. Saunders Company, 1984, RB37, B45.
P. Tjssen, "Practice and Theory of Enzyme Immunoassays", Laboratory Techniques in Biochemistry and Molecular Biology, vol. 15, (New York, Elsevier, 1985), pp. 9-20.
William D. Geoghegan et al., "The application of glucose oxidase-labeled antibodies for the detection of proteins on nitrocellulose", Journal of Immunological Methods, vol. 93, (Nov. 6, 1998), pp. 231-236.
K. Kanai et al., "Variations in effectiveness of antigen retrieval pretreatments for diagnostic immunohistochemistry", Research in Veterinary Science, vol. 64, No. 1 (Jan.-Feb. 1998), pp. 57-61.
Pádraig M. Strappe et al., "Enhancement of immunohistochemical detection of HIV-1 p24 antigen in brain by tyramida signal amplification", Journal of Virological Methods, vol. 67 (Aug. 1997), pp. 103-112.
Emilena Toplikar et al., "Development of an Enzyme Immunoassay for the Detection of Hepatitis B Surface Antigen Employing Monoclonal Antibodies", Journal of Clinical Laboratory Analysis, vol. 7, 1993, pp. 324-328.

(Continued)

Primary Examiner—Jeffrey Stucker
(74) Attorney, Agent, or Firm—McDermott Will & Emery LLP

(57) ABSTRACT

A monoclonal antibody-based Dot-ELISA assay for the rapid detection of animal viruses such as avian influenza virus. The assay includes applying a specimen suspected of containing an animal virus on a porous membrane and treating the specimen with a solution of citric acid or lactic acid and a solution containing a mucolytic agent and a detergent. The treated specimen is then contacted with a primary monoclonal antibody for detecting the virus. If present, the primary moncolonal antibody bind with an antigen of the animal virus specimen. The specimen is contacted with an anti-monoclonal antibody conjugate (secondary antibody) and incubated to facilitate binding of the antigen-bound monoclonal antibody to the conjugate. The bound conjugate and antigen-bound monoclonal antibody is contacted with a coloring reagent to allow visual detection of the presence of the animal virus in the specimen.

10 Claims, No Drawings

OTHER PUBLICATIONS

Program and Abstracts, Congress of the World Veterinary Poultry Association, Jul. 19-23, Co-sponsored by the American Association of Avian Pathologists and the American Veterinary Medical Association.

North Atlantic Poultry Health and Management Conference, Mar. 20-21, 2002, Sheraton Harborside Hotel and Conference Center, Portsmouth, New Hampshire.

Proceedings of the Fifty-Second Western Poultry Disease Conference, Mar. 8-11, 2003, Sacramento, California.

Atmar, R.L., B.D. Baxter, E.A. Dominguez, L. H. Taber., "Comparison of reverse transcription-PCR with tissue culture and other rapid diagnostic assays for detection of type A influenza virus", J Clin Microbiol. 34(10): 2604-6. 1996.

Swayne, David E., Dennis A. Senne and Charles W. Beard, "Avian Influenza", In: A Laboratory Manual for the Identification of Avian Pathogens. Published by The American Association of Avian Pathologists, 4th ed. 1998, pp. 150-155.

Easterday, B. C., Virginia S. Hinshaw, and David A. Halvorson, "Influenza", In: Diseases of Poultry, 10th ed, by B.W. Calnek, H.J. Barnes, C. W. Beard, L.R. McDonald, and Y.M. Saif, Iowa State University Press, Ames, Iowa, pp. 583-605, 1997.

Kodihalli, S., V. Sivanandan, K.V. Nagaraja, S.M. Goyal, D.A. Halvorson, "Antigen-capture enzyme immunoassay for detection of avian influenza virus in turkeys", Am J Vet Res. 54(9):1385-90, Sep. 1993.

Lee, M.S., P.C. Chang, J. H. Shien, M.C. Cheng, H.K. Shieh, "Identification and subtyping of avian influenza viruses by reverse transcription-PCR", Journal of Virol Methods, 97(1-2): pp. 13-22, Sep. 2001.

Martin, S.W., Alan H. Meek, and P. Willeberg, "Veterinary Epidemiology Principles and Methods", In Chapter 5 of Disease Causation: Table 5.3, The chi-square test (McNemar's) applied to differences between two correlated proportions. p. 127. Iowa State University Press, Ames, 1st ed. 1987.

Munich, M., L.P. Nielsen, K.J. Handberg, P.H. Jorgensen, "Detection and subtyping (H5 and H7) of avian type A influenza virus by transcription-PCR and PCR-ELISA", Abstract, Arch Virol. 146(1):, 2001.

Pearson, J.F., and D.A. Senna, "Diagnostic procedures for avian influenza", In Proceedings 2nd International Symposium on Avian Influenza, United States Animal Health Association, Atlanta, GA, pp. 222-227, 1986.

Pregliasco, F., C. Mensi, L. Carnorali, G. Anselimi, "Comparison of RT-PCR with other diagnostic assays for rapid detection of influenza viruses", J Med Virol. 56(2): pp. 168.73, 1998.

Schwabe, C.W., H.P. Riemann, C.E. Franti, "Epidemilogy in Veterinary Practice", In Chapter 5 of Mathematical Approach: Test sensitivity and specificity, pp. :74-75. Philadelphia: Lea & Febiger, 1977.

Thayer, S.G., and C.W. Beard, "Serological Procedures", In: A Laboratory Manual for the Identification of Avian Pathogens, Published by The American Association of Avian Pathologists, 4th ed. 1998.

Waner, J.L, S.J. Todd, H. Shalaby, P. Murphy, L.V. Wall, "Comparison of Directigen FLU-A with viral isolation and direct immunofluorescence for the rapid detection and identification of influenza A virus", J Clin Microbiol. 29(3): 479-82. 1991.

Wang, X, A.E. Castro, M.D. Castro, H. Lu, D. Weinstock, N. Soyster, W. Scheuchenzuber, M. Perdue, "Production and evaluation criteria of specific monoclonal antibodies to the hemagglutinin of the H7N2 subtype of avian influenza virus", J. Vet Diagn Invest. 12(6): 503-9, 2000.

Webster, R.G., and C. H. Campbell, "An inhibition test for identifying the neuraminidase antigen of influenza viruses", Avian Dis. 16: 1057-1068, 1972.

Lu, H., "A Longitudinal Study of a Novel Dot-Enzyme-Linked Immunosorbent Assay for Detection of Avian Influenza Virus", Avian Diseases, Animal Diagnostic Laboratory, Dept. of Veterinary Science, The Penn State University, 47:362-369, 2003.

"New Lab Test for Avian Flu" ARS News Service Agricultural Research Service, USDA Sharon I Feb. 18, 2003, pp. 1-2, http://nps.ars.usda.gov/menu.htm?newsid=2106.

Avian Diseases "A Longitudinal Study of a Novel Dot-Enzyme-Linked Immunosorbent Assay for Detection of Avian Influenza Virus", published by The Pennsylvania State University, Inc., Pub. Date 2003, pp. 361-369.

Avian Diseases "Investigation of H7N2 Avian Influenza Outbreaks in Two Broiler Breeder Flocks in Pennsylvania," published by the Pennsylvania State University. Inc. Pub. 2001-2002, pp. 26-33.

Program and Abstracts, Congress of the World Veterinary Poultry Association, Jul. 19-23, Co-sponsored by the American Association of Avian Pathologists and the American Veterinary Medical Association. (2003).

* cited by examiner

MAB-BASED DOT-ELISA METHOD AND ASSAY KIT FOR THE DETECTION OF VIRUSES

CROSS REFERENCE TO A RELATED APPLICATION

This application claims the benefit of U.S. Provisional Patent Application No. 60/385,841, filed May 31, 2002.

FIELD OF THE INVENTION

The present invention generally relates to methods for detecting and identifying animal viruses present in a clinical and virus cultural specimen with available monoclonal antibodies to the specific virus.

BACKGROUND OF THE INVENTION

Avian influenza is a rapidly spread aerosolized bird disease and rapidly infects flocks or birds when outbreak occurs. Isolation of avian influenza virus (AIV) using embryonating chicken eggs (ECE) has been the standard test, although it is a labor intensive and time consuming procedure. All 15 subtypes of AIV replicate successfully in ECE as measured by hemagglutination (HA) test. The hemagglutination-inhibition (HI) and neuramimidase-inhibition (NI) tests are commonly used to identify each specific subtype of AIV. During the past decade, new methodologies using monoclonal antibodies-based assays and molecular techniques have been evolved and studied in the demonstration of antigens of AIV directly from clinical and field specimens. Although these advanced methods are not yet applicable for routine diagnostic or surveillance purposes, they have been employed in certain circumstances for the identification of AIV in conjunction with virus isolation in ECE. To enhance the rapid detection of AIV in flocks enables the growers and public authorities to better control the rapid spread of disease.

The present invention provides a rapid test for such animal viruses that is accurate and far less costly than conventional testing methods. Isolation of AIV using ECE has been the gold standard to date, but it is a time consuming procedure. The procedure requires at least a minimum of 2 to 3 days to determine a test result. Avian influenza is a vexing problem for poultry producers. Avian influenza infections can range from subclinical with no symptoms, to mild with some production losses, to severe with high rates of illness and death. The present invention is directed to a monoclonal antibody-based dot enzyme-linked immunosorbent assay (MAb-based Dot-ELISA) test which is cheaper and a far more rapid test for detecting such viruses than the procedures and tests described above.

SUMMARY OF THE INVENTION

The object of this invention is to provide a rapid and less costly method for detecting animal viruses. To accomplish the object described above according to the present invention, there is provided a method using a MAb-based Dot-ELISA which comprises:

(a) providing a substrate for performing a monoclonal antibody-based assay;

(b) applying to the substrate a specimen suspected of containing an animal virus;

(c) applying to the substrate a solution containing an organic acid;

(d) applying to the substrate a solution containing a mucolytic agent and a detergent;

(e) contacting the substrate with a primary monoclonal antibody and for a time sufficient to allow the monoclonal antibody and an antigen of said animal virus specimen to bind together to form an antigen-bound primary monoclonal antibody;

(f) contacting the antigen-bound primary monoclonal antibody with an anti-monoclonal antibody conjugate for a time sufficient to facilitate binding of the antigen-bound monoclonal antibody to the conjugate; and (g) applying a color reagent to the substrate, the color reagent capable of binding to the conjugate and developing a colored marking to allow visual detection of the presence of animal virus in the specimen.

A further object of the invention is to provide for a monoclonal body assay kit for the detection and identification of an animal virus comprising a substrate for performing a monoclonal antibody-based assay, a solution of an organic acid, a solution of a detergent and a mucolytic agent, a primary monoclonal antibody for detecting the virus, an anti-monoclonal antibody conjugate, and a coloring reagent.

A still further object of the invention is to provide a solution of an organic acid for removal of non-viral substances containing in a test sample that may cause false positive and a solution of a detergent and a mucolytic agent for virus protein extraction.

It is still a further object of the invention that the method and monoclonal assay kit can be used to detect and identify animal viruses such as AIV, avian infectious bronchitis virus, infectious bursal disease virus, infectious larygotrachitis virus, fowl adenovirus, fowl pox virus, avian reovirus, avian rotavirus, swine influenza virus or equine influenza virus.

Other objects and characteristics of the present invention will become apparent from the further disclosure of the invention.

DETAILED DESCRIPTION OF THE INVENTION

The present invention relates to a MAb-based Dot-ELISA test that specifically detects the proteins associated with an avian virus or other animal virus by using specific monoclonal antibodies to that virus. The procedure and reagents used in the MAb-based Dot-ELISA test for detection of different avian and other animal viruses are identical except the primary monoclonal antibodies, which require homologous specific to a specific virus, are different.

The MAb-based Dot-ELISA test of the present invention detects the AIV directly from clinical and field specimens. The novel MAb-based Dot-ELISA test detects antigens of all AIV subtypes when using group-specific monoclonal antibody (MAb) to AIV nucleic proteins and specifically detects H7N2 subtype when using H7N2 subtype-specific MAb. The MAb-based Dot-ELISA test was specific for AIV as no cross-reactions were obtained with other avian viruses.

The invention is directed to a method for the detection and identification of an animal virus in a specimen using a MAb-based Dot-ELISA test. The method comprises the steps of:

(a) providing a substrate for performing a monoclonal antibody-based assay;

(b) applying to the substrate a specimen suspected of containing an animal virus;

(c) applying to the substrate a solution containing an organic acid;

(d) applying to the substrate a solution containing a mucolytic agent and a detergent;

(e) contacting the substrate with a primary monoclonal antibody and for a time sufficient to allow the monoclonal antibody and an antigen of said animal virus specimen to bind together to form an antigen-bound primary monoclonal antibody;

(f) contacting the antigen-bound primary monoclonal antibody with an anti-monoclonal antibody conjugate for a time sufficient to facilitate binding of the antigen-bound monoclonal antibody to the conjugate; and (g) applying a color reagent to the substrate, the color reagent capable of binding to the conjugate and developing a colored marking to allow visual detection of the presence of animal virus in the specimen.

The animal viruses to be tested include AIV, avian infectious bronchitis virus (IBV), infectious bursal disease virus (IBDV), infectious larygotrachitis virus (ILTV), fowl adenovirus (FAV), fowl pox virus, avian reovirus, avian rotavirus, swine influenza virus or equine influenza virus. It is not intended that the MAb-based Dot-ELISA test should be limited to these particular animal viruses or their accompanying antigens. Rather, it is contemplated that the MAb-based Dot-ELISA test method of the present invention may also be used for the detection of other avian and animal viruses by using available monoclonal antibodies specific to those viruses.

The novel features in MAb-based Dot-ELISA test method involve (i) the treatment solutions A and B, (ii) the selection and use of a substrate, a porous membrane such as nitrocellulose, and (iii) the production and application of specific MAb to specific animal viruses (e.g., AIV H7N2, IBV). The procedure is based on antigen-antibody reaction. Other reagents in the procedure, such as detector block solution, washing solution, enzyme labeled goat anti-mouse IgG conjugate (secondary antibody), and alkaline phosphatase substrate, are commercially available. These reagents, while available for use in the MAb-based Dot-ELISA test procedure, are not specific for the detection of viruses.

The MAb-based Dot-ELISA test specifically detects the proteins associated with AIV and IBV. The novel MAb-based Dot-ELISA test method of the invention is a rapid and effective diagnostic test. One individual can test up to 100 samples in one run within two hours.

The MAb-based Dot-ELISA test method of the present invention detects live virus antigens, as well as inactivated antigens of AIV, directly from clinical and field specimens. The sensitivity of the MAb-based Dot-ELISA test for AIV detection ranges from 25–70% while the specificity ranges from 80–100% in testing various clinical and field specimens in comparison with virus isolation using ECE. Sensitivity is a test value that measures the proportion of animals that are truly infected or the proportion of specimens that are truly positive. Specificity is a test value that measures the proportion of animals that are truly not infected or the proportion of specimens that are truly negative. Sensitivity and Specificity are calculated based on a 2×2 contiguous table which classifies test results of a diagnostic test (e.g., MAb-based Dot-ELISA test) by a standard test (e.g., virus isolation in ECE) as follows:

| | | Animal Status | | | |
|---|---|---|---|---|---|
| | | Infected | Non-infected | Total | |
| Test Positive | + | a | b | a + b | Sensitivity = a/(a + c) |
| Test Negative | − | c | d | c + d | Specificity = d/(b + d) |
| | Total | a + c | b + d | N | |

Hemagglutination (HA) and hemagglutination-inhibition (HI) are standard tests used for identification and serotyping of AIV after the virus is isolated in ECE or tissue cultures. The MAb-based Dot-ELISA test method agrees with HA and HI tests in 100% sensitivity and 100% specificity in testing AIV from ECE or tissue culture materials.

The MAb-based Dot-ELISA test method detects AIV antigens in allantoic fluid samples (virus culture in ECE) that contain a concentration as low as 0.4 HA unit in a 5 μl sample. The MAb-based Dot-ELISA test method is specific for AIV and no cross-reactions are obtained with other avian viruses. The MAb-based Dot-ELISA test method is highly sensitive and comparable to a commercial Directigen® test in the detection of AIV. The Directigen® test is designed to detect influenza type A viruses in humans and it also can be used to detect AIV since AIV belongs to influenza type A viruses. The Directigen® test has been used for AIV detection during AIV outbreaks in recent years, but it is a very costly test, about $18 per test. Because of the cost, it is not feasible for mass testing during outbreaks or routine surveillance as one device for one test sample. Furthermore, the Directigen® test only detects common antigens associated with AIV and does not apply for subtyping of the 15 H subtypes of AIV.

The MAb-based Dot-ELISA test method of the present invention using MAb to IBV has also been successfully applied for the detection and identification of IBV. It achieves 100% sensitivity and 100% specificity in comparison with an indirect fluorescent antibody test (IFA). The IFA is used as a standard diagnostic test for the detection and identification of IBV from a specimen-inoculated ECE. IBV containing in a diagnostic specimen generally requires 3 to 4 serial passages in ECE to be detectable by the IFA. The MAb-based Dot-ELISA test of the present invention detects IBV 1 or 2 passages, far earlier than the IFA.

The testing method of the present invention includes a nitrocellulose membrane and Dot-ELISA standard reagents such as a detector block solution, a washing solution, an enzyme labeled goat anti-mouse IgG (secondary antibody), and an alkaline phosphatase substrate of 5-bromo-4-chloro-3-indolyl-phosphate/nitroblue tetrazolium (BCIP/NBT). The MAb-based Dot-ELISA test method includes two additional treatment solutions: solution A comprising an organic acid for removal of non-viral substances containing in a test sample that may cause false positive and solution B comprising a detergent and a mucolytic agent for virus protein extraction.

The organic acid of solution A can be citric acid or lactic acid. A citric acid solution is preferred and can be prepared by mixing 150 mM citric acid in distilled water.

Solution B is prepared by mixing 1.5% (v/v) mucolytic agent, 6% (v/v) detergent and 0.2% (w/v) sodium azide. The mucolytic agent can be dithiothreitol, N-acetyl-L-cysteine or bromhexine hydrochloride. The detergent can be an octoxynol (such as Triton™ X-100, Triton™ X-114 or Igepal™ CA-630), or an octylglucoside (such as octyl-β-D-glucopyranoside), or other similar non-ionic detergent.

The following are representative examples of using the novel MAb-based Dot-ELISA test method of the present invention for the detection of animal viruses. These examples are not to be considered as limiting the scope of the invention in any manner.

EXAMPLE 1

AIV subtype-specific MAb to H7N2 were produced at the Monoclonal Laboratory at Penn State University. The general or group MAb to all subtypes of AIV were provided by Dr. Michael L. Perdue of ARS, USDA, Beltsville, Md.

Reference strains of AIV subtypes H3N2, H4N8, H5N3, H6N8, H7N2 and H9N1 stored in The Pennsylvania State University's Animal Diagnostic Laboratory were used for sensitive and specific testing of the MAb-based Dot-ELISA test in the detection of AIV. All 15 subtypes H1 through H15 of AIV were tested at the National Veterinary Services Laboratories in Ames, Iowa. Other avian viruses, including IBV, ILTV, PMV, FAV, fowl pox virus, avian reovirus and avian rotavirus, were used for specific testing of the MAb-based Dot-ELISA test for AIV.

The novel MAb-based Dot-ELISA test procedure of the present invention comprises the following steps:

(1) Preparing test strips (50–60 mm×10 mm) of nitrocellulose membrane, placing the test strips on chromatography paper (20×20 cm), and then applying test samples to the strips (5 µl per sample, 5–6 samples per strip), and allowing the test strips to air dry.

(2) Treating the test strips with solution A comprising 150 mM citric acid prepared in distilled water for approximately 5 minutes.

(3) Washing the test strips with a wash solution two times, for about 30–60 seconds each time.

(4) Treating the strips with solution B comprising 1.5% (v/v) dithiothreitol, 6% (v/v) Triton™ X-100 and 0.2% sodium azide for approximately 5 minutes and washing twice as described in step (3).

(5) Applying a block solution to the strips, incubating for approximately 10 to 30 minutes and then allowing the strips to air dry.

(6) Applying appropriate monoclonal antibodies for detecting a specific virus to the strips and incubating for about 15–30 minutes.

(7) Washing the test strips with washing solution three times, approximately 2 minutes each time.

(8) Adding secondary antibody of goat anti-mouse IgG conjugate to the strips and incubating for approximately 15–30 minutes.

(9) Washing the strips as described in step (7).

(10) Adding BCIP/NBT coloring reagent and incubating for approximately 5–10 minutes in the dark for color development. If the antigen is present, a purple color will indicate the presence of the virus. The intensity of the purple color will indicate the relative concentration of the antigen in the specimen. The reaction of the coloring reagent can be stopped by adding distilled $H_2O$ or tap water when a clear purple dot develops on a positive control sample. If the antigen is absent, no color develops.

All reactions are conducted at ambient temperature in clean Pitch dishes. The test strips are placed on chromatography paper to air dry before and after each reaction.

EXAMPLE 2

A combination of MAb-based Dot-ELISA test and virus isolation in ECE was successfully used for the rapid laboratory diagnosis of AIV within 24 hours during the 2001/02 outbreak in Pennsylvania. This study was conducted at The Pennsylvania State University's Animal Diagnostic Laboratory. Clinical and field specimens including tracheal swabs, cloacal swabs, environmental swabs and watery manure samples were collected from AIV affected and suspicious flocks and processed with viral transfer medium. These specimens were screened first for the presence of antigens of AIV by the MAb-based Dot-ELISA test, and then were inoculated into ECE for virus isolation following standard procedures with the modification of daily withdrawing of allantoic fluid samples. After 20–24 hours, and again 40–48 hours, 0.2–0.5 ml of allantoic fluid was drawn from the ECE that had been inoculated with a specimen which was positive for AIV by MAb-based Dot-ELISA test or from a case clinically suspicious for AIV infection. After allantoic fluid samples were drawn, the ECE were resealed and placed beck to egg incubator for continuous incubation up to 72 to 96 hours. The early incubation allantoic fluid samples were tested for AIV by the MAb-based Dot-ELISA test and hemagglutination (HA) test.

Among 7 flocks affected by AIV during the 2001/02 outbreak in Pennsylvania, the MAb-based Dot-ELISA test detected AIV directly from clinical specimens before virus isolation from 2 broiler breeder flocks, and 4 of 5 broiler flocks. The presence of AIV was confirmed by virus isolation in ECE within 24 hours by means of the modified procedure.

Findings in this study showed that the H7N2 virus present in a clinical specimen grew rapidly in ECE and yielded sufficient HA titers for AIV identification within 24 hours post inoculation if the specimen was positive or suspicious for AIV by the MAb-based Dot-ELISA test. The combination of AIV screening test by MAb-based Dot-ELISA test and virus isolation in ECE provides a rapid and effective laboratory diagnosis of AIV during an outbreak.

The MAb-based Dot-ELISA test is a rapid same day test and comparable to the commercial Directigen® test in the detection of AIV antigens from clinical and field specimens when group specific MAb to AIV nucleic proteins are utilized. The MAb-based Dot-ELISA test also specifically detects H7N2 subtype of AIV when using H7N2 subtype-specific MAb.

EXAMPLE 3

The MAb-based Dot-ELISA test was also evaluated for its ability to detect and antigenically characterize IBV and was compared to that of established ECE and indirect IFA procedures. IBV isolated in ECE from tracheal and rectal swabs collected from commercial layer flocks (and/or SPF sentinels placed in flocks) experiencing egg production and/or shell quality problems in Pennsylvania were used for this procedural evaluation and comparison.

Of 81 field samples tested, 73, 75 and 78 samples were found to contain IBV antigen by IFA, by characteristic chicken embryo lesions assay and by the MAb-based Dot-ELISA test, respectively. Seventy one of 81 samples assayed were positive by all three laboratory procedures. Statistical comparisons of these results strongly suggest that the procedures are equally sensitive in detecting IBV in field samples. A number of false positive (3 Dot-ELISA; 2 IFA) and negative (4 IFA) reactions were identified. Additionally, statistical comparisons of the three different procedures to demonstrated that MAb-based Dot-ELISA test was significantly more sensitive than IFA (P<0.01) and chicken embryo lesion (P<0.001) assays.

Comparative Results

The method of the present invention provides a low cost and more rapid determination of viruses than available commercial kit. By way of example, a comparison to a commercial Directigen® is described below.

A commercial Directigen® kit for the direct detection of human influenza A antigen is manufactured by Becton Dickinson Microbiology Systems in Cockeysville. Md. and distributed by VWR Scientific Products Corporation. The test specimens used for both MAb-based Dot-ELISA test and Directigen® test were tracheal swabs, cloacal swabs, and manure samples. Other environmental samples were collected from experimentally H7N2 infected SPF chickens, H7N2 positive flocks of field outbreak, and routine AIV surveillance submissions. All the clinical and field samples were processed with viral transfer medium not containing serum and filtered through 0.45 μm filters. These specimens were first tested for the presence of antigens of AIV by the MAb-based Dot-ELISA test using AIV group- or subtype-specific MAb and then were inoculated into embryonating chicken eggs for virus isolation. The virus isolation results were determined by the HA and HI tests.

The MAb-based Dot-ELISA test was found to be specific for all subtypes of AIV by using group-specific MAb to AIV nucleic protein. The H7N2 MAb was specific for H7N2 subtype and had no reaction to other subtypes. Reactions of the MAb-based Dot-ELISA test using AIV group and subtype-specific MAb did not occur with other viruses tested, namely, IBV, ILTV, PMV, FAV, fowl pox virus, avian reovirus and avian rotavirus.

The MAb-based Dot-ELISA test was highly sensitive and comparable to the commercial Directigen® test in the detection of AIV. Both assays were evaluated using two-fold serial dilutions of HA unites of H5N3 reference strain and field isolates of H7N2 virus obtained in Pennsylvania poultry in 1997 and 2001. The MAb-based Dot-ELISA test detected AIV antigens in allantoic fluid specimens as low as 0.4 HA unit using a 5 μl sample per test. The reactions increased in intensity as the HA units were increased. Reactions were not clearly observed on the test specimens which contained less than 0.4 HA unit. By comparison, the Directigen® test detected the same concentration of 0.4 HA unit of allantoic fluid specimens. The results are summarized in Table 1 below.

TABLE 1

Comparison of the sensitivities of the MAb-based Dot-ELISA test and Directigen ® test in detection of AIV in allantoic fluid samples measured by HA units

| Two-fold dilutions of AIV[a] HA units in AF sample | MAb-based Dot-ELISA test using AIV group-specific MAb | Directigen ® test |
|---|---|---|
| 6.4 | +++ | +++ |
| 3.2 | +++ | +++ |
| 1.6 | ++ | ++ |
| 0.8 | + | + |
| 0.4 | + | + |
| 0.2 | − | − |
| 0.1 | − | − |
| 0.05 | − | − |

[a]The AIV subtypes used for this test including 2 field isolates of H7N2 (PA/H7N2/chicken/3779-2/97 and PA/H7N2/broiler/8015/01) and 2 reference strains of H5N3 and H3N2.

Sensitivity and Specificity of MAb-Based Dot-ELISA Test

Sensitivity (Se) and specificity (Sp) of the MAb-based Dot-ELISA test in the detection of AIV from clinical and field specimens are set forth in Table 2 below. The Table is divided into results for four trials. Three trials were directed to SPF chickens infected with H7N2 virus. The fourth trial is directed to H7N2 outbreak in broiler chickens in Pennsylvania in 2001/02.

Three clinical trials of SPF chickens infected with H7N2 virus were conducted as models for Se and Sp evaluation of the MAb-based Dot-ELISA test for screening a large number of samples to detect antigens of AIV. Se and Sp of the MAb-based Dot-ELISA test in the detection of AIV were calculated using a 2×2 contiguous table set forth above, in which the virus isolation results in ECE were used as a gold standard test. The MAb-based Dot-ELISA test detected virus antigens directly from tracheal, cloacal and environmental swabs, in which the Se ranged from 25% to 70% and the specificity ranged from 80% to 100% in testing various clinical specimens. An average of 45–57% Se and 85–90% Sp was obtained in calculation of total test specimens together per trial. The results are summarized in Trials 1–3 of Table 2.

In testing field specimens collected from affected broiler flocks of the 2001/02 AI outbreak in Pennsylvania, the MAb-based Dot-ELISA test obtained over 40–88% or an average of 68% of Se, and 80–100% or an average of 90% of Sp in the detection of AIV directly from tracheal swabs and cloacal swabs of live birds, lung, and body exudative fluids of dead birds, manure and environmental samples in affected chicken houses. The results are summarized in Trial 4 of Table 2 below. The Dot-ELISA yielded 100% Se and 100% Sp in testing allantoic fluid samples after the clinical and field specimens were passaged through embryonating chicken eggs for virus isolation. The MAb-based Dot-ELISA test was highly sensitive for the detection of AIV in allantoic fluids and agreed with the HA/HI test for AIV identification.

TABLE 2

Sensitivity (Se) and specificity (Sp) of the MAb-based Dot-ELISA test in the detection of AIV from tracheal, cloacal and environmental swabs of experimentally infected SPF chickens and a field AI outbreak in broiler chickens.

| AIV clinical Trials and type of specimens | Number of specimens | Se % (a/(a + c)) | Sp % (d/(b + d)) |
|---|---|---|---|
| 2.1. Trial-1: 40 five-week-old SPF chickens inoculated with AIV (PA/H7N2/chicken/3779-2/97) | | | |
| Tracheal swabs of group A[a] and B[b] combined | 37 | 25.00 (5/25) | 100 (17/17) |
| Cloacal swabs of group A and B combined | 93 | 70.97 (22/31) | 82.26 (51/62) |
| Environmental swabs of group A and B combined | 45 | 68.42 (13/19) | 84.62 (22/26) |
| Total swabs tested[c] | 175 | 57.14 (40/70) | 85.71 (90/105) |
| Allantoic fluid samples[d] | 175 | 100 (70/70) | 100 (105/105) |
| 2.2. Trial-2: 30 ten-week-old SPF chickens inoculated with AIV (PA/H7N2/chicken/3779-2/97) | | | |
| Tracheal swabs of group A[a] | 154 | 41.67 (10/24) | 90.77 (118/130) |
| Tracheal swabs of group B[b] | 151 | 44.44 (12/27) | 86.29 (107/124) |

TABLE 2-continued

Sensitivity (Se) and specificity (Sp) of the MAb-based Dot-ELISA test in the detection of AIV from tracheal, cloacal and environmental swabs of experimentally infected SPF chickens and a field AI outbreak in broiler chickens.

| AIV clinical Trials and type of specimens | Number of specimens | Se % (a/(a + c)) | Sp % (d/(b + d)) |
|---|---|---|---|
| Cage swabs of group A and B | 29 | 40.00 (4/10) | 94.74 (18/19) |
| Filter dust swabs of group A and B | 23 | 62.50 (5/8) | 93.33 (14/15) |
| Total swabs tested[c] | 357 | 44.93 (31/69) | 89.24 (257/288) |
| Allantoic fluid samples[d] | 357 | 100 (169/169) | 100 (257/257) |
| 2.3. Trial-3: 26 fourteen-week-old SPF chickens inoculated with AIV (PA/H7N2/chicken/3779-2/97) | | | |
| Tracheal swabs of group A[a] | 115 | 47.83 (11/23) | 91.30 (84/92) |
| Tracheal swabs of group B[b] | 117 | 37.04 (10/27) | 86.67 (78/90) |
| Cage swabs of group A and B | 29 | 50.00 (5/10) | 89.47 (17/19) |
| Filter dust swabs of group A and B | 20 | 70.00 (7/10) | 100 (10/10) |
| Total swabs tested[c] | 281 | 47.14 (33/70) | 89.57 (189/211) |
| Allantoic fluid samples[d] | 281 | 100 (70/70) | 100 (211/211) |
| 2.4. The 2001/02 AIV (H7N2) outbreak in broiler chickens in Pennsylvania | | | |
| Tracheal swabs | 40 | 80.77 (21/26) | 100 (14/14) |
| Cloacal swabs | 34 | 40.00 (10/25) | 88.89 (8/9) |
| Environmental swabs | 39 | 88.89 (16/18) | 80.95 (17/21) |
| Total swabs tested[c] | 113 | 68.12 (47/69) | 90.91 (40/44) |
| Allantoic fluid samples[d] | 113 | 100 (69/69) | 100 (44/44) |

[a] Group A birds in each of the three trials received a volume of 0.5 ml of 50,000 chicken embryo lethal dose 50% ($ELD_{50}$) per bird via a combination of oral, eye and nasal droplets.
[b] Group B birds in each of the three trials received a volume of 0.5 ml of 500,000 chicken embryo lethal dose 50% ($ELD_{50}$) per bird via a combination of oral, eye and nasal droplets.
[c] Total swab samples tested by the MAb-based Dot-ELISA test before inoculation to ECE.
[d] Allantoic fluid samples tested by the MAb-based Dot-ELISA test after one passage of the swab samples in ECE.

Comparison of Sensitivity and Specificity Data for the MAb-Based Dot-ELISA Test and Directigen® Tests No significant difference was seen between the MAb-based Dot-ELISA test and Directigen® test for their Se and Sp in the detection of AIV. Both assays detected AIV directly from clinical samples of tracheal, cloacal and environmental swabs from experimentally infected SPF chickens and 2001/02H7N2 outbreaks in broiler flocks in Pennsylvania. The results are summarized in Tables 3 and 4 below.

TABLE 3

Comparison of the MAb-based Dot-ELISA test and Directigen® test in the detection of AIV directly from clinical specimens of tracheal, cloacal and environmental swabs collected from experimentally infected SPF chickens (AI trial-I).

3.1. Sensitivity (Se) and (specificity) Sp of MAb-based Dot-ELISA and Directigen® in testing a sample group of samples.

| | | Virus Isolation in ECE | | | |
|---|---|---|---|---|---|
| | | + | − | Total | |
| Dot-ELISA | + | 9 | 1 | 10 | Se = 9/21 = 42.86% |
| | − | 12 | 7 | 19 | Sp = 7/8 = 87.50% |
| | Total | 21 | 8 | 29 | |
| Directigen® | + | 8 | 1 | 9 | Se = 8/21 = 38.10% |
| | − | 13 | 7 | 20 | Sp = 7/8 = 87.50% |
| | Total | 21 | 8 | 29 | |

3.2. Comparison of the MAb-based Dot-ELISA test and Directigen® test by the McNemar's chi-square test.

| | | Directigen® test | | |
|---|---|---|---|---|
| | | + | − | Total |
| Dot-ELISA | + | 9 | 1 | 10 |
| | − | 0 | 19 | 19 |
| | Total | 9 | 20 | 29 |

$X^2 = (|0 − 1| − 1)^2/(0 + 1) = 0$
Since $X^2 = 0 < X^2_{1, 0.95} = 3.84$, thus $p < 0.05$
Therefore, the two assays are not significantly different.

TABLE 4

Comparison of the MAb-based Dot-ELISA test and Directigen® test in the detection of AJY from clinical specimens of tracheal, cloacal and environmental swabs collected from broiler flocks affected with H7N2 virus during the 2001/02 outbreaks in Pennsylvania.

4.1. Sensitivity (Se) and specificity (Sp) of MAb-based Dot-ELISA and Directigen® in testing a sample group of samples.

| | | Virus Isolation in ECE | | | |
|---|---|---|---|---|---|
| | | + | − | Total | |
| Dot-ELISA | + | 43 | 4 | 47 | Se = 43/69 = 62.32% |
| | − | 26 | 40 | 66 | Sp = 40/44 = 90.91% |
| | Total | 69 | 44 | 113 | |
| Directigen® | + | 40 | 2 | 42 | Se = 40/69 = 57.97% |
| | − | 29 | 42 | 71 | Sp = 42/44 = 95.45% |
| | Total | 69 | 44 | 113 | |

TABLE 4-continued

Comparison of the MAb-based Dot-ELISA test and Directigen ® test in the detection of AJY from clinical specimens of tracheal, cloacal and environmental swabs collected from broiler flocks affected with H7N2 virus during the 2001/02 outbreaks in Pennsylvania.
4.2. Comparison of the MAb-based Dot-ELISA test and Directigen ® test by the MeNemar's chi-square test

|  |  | Directigen ® test | | |
|---|---|---|---|---|
|  |  | + | − | Total |
| Dot-ELISA | + | 41 | 6 | 47 |
|  | − | 1 | 65 | 66 |
|  | Total | 42 | 71 | 113 |

$X^2 = (|1 - 6| - 1)^2/(1 + 6) = 2.28$
Since $X^2 = 2.28 < X^2_{1,\ 0.95} = 3.84$, thus $p < 0.05$
Therefore, the two assays are not significantly different.

The results of comparison studies between the MAb-based Dot-ELISA test and Directigen® test indicate that both assays possessed equivalent Se and Sp and thus both assays are equally sensitive and specific in the detection of AIV. However, both assays in the AIV detection were less sensitive than virus isolation in ECE (Tables 3.1 and 4.1). This is because ECE can amplify AIV to a detectable titer during a period of 2-to-3 days of incubation although an inoculum contains a very low concentration of the virus, whereas the MAb-based Dot-ELISA test and Directigen® test do not amplify AIV. Thus, they require a minimum concentration of virus particles (e.g., 0.4 HA unit) presenting in a test specimen to produce a visualized positive reaction.

Nonetheless, specimens collected from AIV-infected birds during an outbreak shall have adequate virus particles to be detectable by the MAb-based Dot-ELISA test or Directigen® test. The MAb-based Dot-ELISA test results in testing clinical and field specimens from AIV-infected birds in this study indicated that between 45% and 68% in average of such specimens containing AIV (H7N2) were successfully identified as AIV positive by the MAb-based Dot-ELISA test (Table 2). Specifically in trial 1 (Table 2.1), the MAb-based Dot-ELISA test detected over 70% of AIV positive cloacal swabs, but only 25% of AIV positive tracheal swabs. The low 25% Se in testing tracheal swabs was because the tracheal swabs were collected after two weeks post inoculation, when the virus concentration in tracheas became very low; whereas cloacal swabs were collected during the period that birds actively released virus through intestines and thus the high 70% Se was achieved. Therefore, a sufficient number of samples and early sampling of various sources during an outbreak are essential for the MAb-based Dot-ELISA test to successfully detect AIV and achieve a high Se in the detection.

Specificity of the MAb-Based Dot-ELISA Test in Testing of AIV Surveillance Samples AIV surveillance samples submitted to the laboratory of the present inventor are routinely processed for virus isolation using ECE and are also tested for the presence of AIV antigens by the MAb-based Dot-ELISA test. From April to December 2001, a total number of 1589 AIV surveillance samples in 32 submissions have been tested by both methods. The 1589 samples were all negative for virus isolation in ECE, 13 out of the 1589 samples in 7 submissions had positive reactions by the MAb-based Dot-ELISA test. The specificity of the MAb-based Dot-ELISA test for identification of AIV negative samples among these 32 submissions ranged from 92% to 100%, or 99.18% of mean Sp, or 0.82% (13/1589) false positive in comparison with virus isolation in ECE. The results are summarized in Table 5 below.

TABLE 5

Specificity (Sp) of the MAb-based Dot-ELISA test on AIV surveillance samples in the identification of AIV negative specimens in comparison to virus isolation in ECE

| Serial No. of submissions | Number of samples | No. of positives by Dot-ELISA | No. of positives by virus isolation | Dot-ELISA Specificity (%) |
|---|---|---|---|---|
| 1 | 51 | 0 | 0 | 100 |
| 2 | 70 | 0 | 0 | 100 |
| 3 | 42 | 0 | 0 | 100 |
| 4 | 70 | 2 | 0 | 97.14 |
| 5 | 58 | 0 | 0 | 100 |
| 6 | 55 | 0 | 0 | 100 |
| 7 | 45 | 0 | 0 | 100 |
| 8 | 37 | 0 | 0 | 100 |
| 9 | 47 | 0 | 0 | 100 |
| 10 | 61 | 0 | 0 | 100 |
| 11 | 47 | 0 | 0 | 100 |
| 12 | 70 | 1 | 0 | 98.57 |
| 13 | 45 | 1 | 0 | 97.77 |
| 14 | 55 | 0 | 0 | 100 |
| 15 | 35 | 0 | 0 | 100 |
| 16 | 35 | 0 | 0 | 100 |
| 17 | 77 | 0 | 0 | 100 |
| 18 | 31 | 0 | 0 | 100 |
| 19 | 30 | 0 | 0 | 100 |
| 20 | 36 | 1 | 0 | 97.22 |
| 21 | 54 | 0 | 0 | 100 |
| 22 | 30 | 0 | 0 | 100 |
| 23 | 39 | 0 | 0 | 100 |
| 24 | 40 | 0 | 0 | 100 |
| 25 | 40 | 3 | 0 | 92.51 |
| 26 | 43 | 1 | 0 | 97.67 |
| 27 | 52 | 0 | 0 | 100 |
| 28 | 22 | 0 | 0 | 100 |
| 29 | 10 | 0 | 0 | 100 |
| 30 | 58 | 0 | 0 | 100 |
| 31 | 24 | 0 | 0 | 100 |
| 32 | 120 | 4 | 0 | 96.67 |
| Total | 1589 | 13 | 0 | 99.18 |

Findings indicate that the MAb-based Dot-ELISA test is highly sensitive in detecting antigens of AIV. It detected AIV in allantoic fluids that contained a concentration as low as 0.4 HA units. The MAb-based Dot-ELISA test using group-specific monoclonal antibody to AIV nucleic protein detected AIV hemagglutinin subtypes H3 through H9 tested. A subtype-specific MAb to H7N2 virus specifically reacted with its homologous H7N2 subtype and had no cross-reaction to other subtypes of AIV. The availability of monoclonal antibody to AIV subtype H7 allows the MAb-based Dot-ELISA test to single out a virulent subtype rapidly from other virulent AIV strains.

The MAb-based Dot-ELISA test agreed with HA and HI tests for AIV identification using allantoic fluids after clinical specimens were passed through ECE. Allantoic fluids harvested from ECE were highly sensitive by the MAb-based Dot-ELISA test and its results were the same to the HA and HI tests for AIV identification. Therefore, some substances from fecal materials created non-specific reactions on the MAb-based Dot-ELISA test strips would be verified as false positives after they were passed through ECE. On the other hand, a positive reaction by the MAb-based Dot-ELISA test, but negative for virus isolation in ECE, may be a true positive for AIV since the MAb-based Dot-ELISA test detects AIV antigens of both live and dead viruses.

Furthermore, the novel MAb-based Dot-ELISA test can be effectively used as a rapid screening and diagnostic test to identify AIV in various sources of surveillance samples and clinical diagnostic specimens. Although the MAb-based Dot-ELISA test can yield false positives under certain circumstances when test samples are composed of dirty substances or chemicals such as dark diarrhea-like manure samples, very bloody tracheal swabs, cloacal swabs containing heavy diarrhea-like manure or environmental swabs containing chemical disinfectants, false positive reactions from these kinds of samples can be ruled out by using clean and quality samples. The Directigen® test also yielded false positive results in this study (Table 3.1 and 4.1). Although the causative substances are not clearly understood, it appears that specimens containing biological or bacterial components or certain chemical substances likely cause false positive reactions in both MAb-based Dot-ELISA test and Directigen® test. The optimal samples for the MAb-based Dot-ELISA test are tracheal and cloacal swabs from suspicious or affected birds, fresh watery wet droppings and chicken house dust. The MAb-based Dot-ELISA test is a same-day test and feasible for mass testing, an individual can screen up to 100 clinical samples in one run within few hours. The MAbs-based Dot-ELISA test significantly improved the ability to rapidly detect antigens of AIV during a field outbreak thus enhancing the ability to control spread, and it has great economic potential in long-term prevention and control of AIV outbreaks.

The novel monoclonal antibody-based MAb-based Dot-ELISA test can be effectively used as a rapid screening and diagnostic test to identify animal viruses in different kinds of surveillance samples and clinical diagnostic specimens. This is a same-day test that can be conducted on site. An individual can screen up to 100 clinical samples in one run within two hours. Although the MAb-based Dot-ELISA test can yield false positives to certain kinds of field specimens composed of dirty substances or chemicals under certain circumstances, true positive reactions can be determined with clean and quantity samples. The optimal samples for the MAb-based Dot-ELISA test are tracheal and cloacal swabs from suspicious or affected birds and other animals, fresh watery wet droppings and chicken house dust.

The MAb-based Dot-ELISA test significantly improves the ability to rapidly detect antigens of animal viruses. It can be applied in mass testing during a field outbreak, or it can be used for routine surveillance. The MAb-based Dot-ELISA test method of the present invention costs less than $0.50 per test. Its sensitivity and specificity in the detection of AIV, for instance, are comparable to the commercial Directigen® kit, which costs over $18.00 per test. The MAb-based Dot-ELISA kit of the present invention has great economic potential in the prevention and control of outbreaks involving animal viruses.

While the invention has been particularly shown and described with reference to preferred embodiments thereof, it will be understood by those skilled in the art that various alterations in form and detail may be made therein without departing from the spirit and scope of the invention.

What is claimed is:

1. A method for detecting a virus in a field or clinical specimen, said method comprising the following steps in sequential order:

(a) obtaining said field or clinical specimen suspected of containing the virus, (b) treating the specimen with a solution consisting essentially of an organic acid to remove non-viral substances, (c) treating the specimen with a solution containing a mucolytic agent and a detergent to extract antigens, and (d) performing a monoclonal antibody-based Dot-ELISA assay to detect an antigen of the virus.

2. The method of claim 1, wherein the organic acid is citric acid or lactic acid.

3. The method of claim 1 wherein the mucolytic agent is selected from the group consisting of dithiothreitol, N-acetyl-L-cysteine, and bromhexine hydrochloride, and the detergent is selected from the group consisting of an octoxynol and an octylglucoside.

4. The method of claim 3, wherein the organic acid is citric acid, the mucolytic agent is dithiothreitol and the detergent is octoxynol.

5. The method of claim 4, wherein the solution of step (c) further includes sodium azide.

6. The method as in any one of claims 1, 2, and 3–5, wherein the virus is the avian influenza virus (AIV).

7. The method as in any one of claims 1, 2, and 3–5, wherein the virus is an avian influenza virus selected from subtypes H1 through H15.

8. The method as in any one of claims 1, 2, and 3–5, wherein the virus is an avian influenza virus having subtype H5 or H7.

9. The method of claim 1, wherein the virus comprises avian influenza virus, avian infectious bronchitis virus, infectious bursal disease virus, infectious larygotrachitis virus, fowl adenovirus, fowl pox virus, avian reovirus, avian rotavirus, swine influenza virus or equine influenza virus.

10. The method of claim 1, further including a washing step between steps (b) and (c).

* * * * *

UNITED STATES PATENT AND TRADEMARK OFFICE
CERTIFICATE OF CORRECTION

PATENT NO.        : 7,083,912 B2
APPLICATION NO.   : 10/448333
DATED             : August 01, 2006
INVENTOR(S)       : Huanguang Lu Page 1 of 1

It is certified that error appears in the above-identified patent and that said Letters Patent is hereby corrected as shown below:

On the Title page,

Under section "(73) Assignee ", insert – ( * ) Notice: This invention was made with support from the government under the USDA Hatch Act No. PN01607. The Government may have certain rights in the invention. –

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,083,912 B2 | Page 1 of 1 |
| APPLICATION NO. | : 10/448333 | |
| DATED | : August 1, 2006 | |
| INVENTOR(S) | : Huanguang Lu | |

It is certified that error appears in the above-identified patent and that said Letters Patent is hereby corrected as shown below:

Col. 1, line 16 insert --This invention was made with government support under Hatch Act Project No. PEN01607, awarded by the United States Department of Agriculture. The Government has certain rights in the invention.--

Signed and Sealed this

Twenty-seventh Day of January, 2009

JOHN DOLL
*Acting Director of the United States Patent and Trademark Office*